United States Patent [19]
Hubbard et al.

[11] Patent Number: 5,248,293
[45] Date of Patent: Sep. 28, 1993

[54] TETHERED MEDICAL RESTRAINT DEVICE

[75] Inventors: Robert P. Hubbard, East Lansing; Robert L. Boughner, Lansing, both of Mich.

[73] Assignee: Biomechanical Design, Inc., East Lansing, Mich.

[21] Appl. No.: 784,571

[22] Filed: Oct. 29, 1991

[51] Int. Cl.$^5$ .............................................. A61F 5/00
[52] U.S. Cl. ........................................ 602/17; 602/18; 602/19; 606/241; 128/875
[58] Field of Search ...................... 602/17, 18, 19; 128/874, 875, 870, 869; 606/241

[56] References Cited

U.S. PATENT DOCUMENTS

| | | | |
|---|---|---|---|
| 1,803,556 | 5/1931 | Nugent | 602/19 |
| 3,099,261 | 7/1963 | Doss et al. | |
| 3,170,659 | 2/1965 | Wood, Jr. | |
| 3,359,976 | 12/1967 | Laval, Jr. | 602/17 |
| 3,376,064 | 4/1968 | Jackson | |
| 3,397,688 | 8/1968 | Gottfried | |
| 3,522,804 | 8/1970 | Towbin | |
| 3,922,034 | 11/1975 | Eggert | |
| 4,339,151 | 7/1982 | Riggs | |
| 4,451,932 | 6/1984 | Wagemann et al. | |
| 4,477,041 | 10/1984 | Dunne | |
| 4,508,294 | 4/1985 | Lorch | |
| 4,592,523 | 6/1986 | Herndon | |
| 4,638,510 | 1/1987 | Hubbard | |
| 4,664,341 | 5/1987 | Cummings | |
| 4,718,412 | 1/1988 | Nesbitt | |
| 4,899,736 | 2/1990 | Nesbitt | 128/870 |
| 4,903,711 | 2/1990 | Gunther | |
| 5,109,835 | 5/1992 | McDonald et al. | 606/241 |

FOREIGN PATENT DOCUMENTS

| | | | |
|---|---|---|---|
| 2259863 | 12/1972 | Fed. Rep. of Germany | 128/75 |
| 656079 | 8/1951 | United Kingdom | |
| 978422 | 12/1964 | United Kingdom | |

Primary Examiner—Richard J. Apley
Assistant Examiner—Lynne A. Reichard
Attorney, Agent, or Firm—Ian C. McLeod

[57] ABSTRACT

A support device (10) intended for use by people who suffer from neck dysfunction resulting in loss of head control is described. The support device is designed to support the head while reducing undesirable head motions relative to the torso. The support device includes a stiff support means mounted on the torso such as a yoke (13) worn over the shoulders and the upper torso and a mast (11) that extends upward from the yoke, behind the wearer's head to a rear portion of the head at a height approximately equal to the head's center of gravity (approximately eye level). A head harness (30) is worn on the head. A tether system (20), consisting of one or more tethers (25), is attached between a slider line (21) mounted on the head harness and a portion of the mast, adjacent the rear portion of the head of the person. The head harness connects the head harness to the mast to couple the head and the torso. Variations of the tethering system provide any desired degree of head mobility from almost total immobilization to loose support. Another embodiment of the support device (90) includes a yoke (91) worn over the torso and an integral mast (93) that extends upward to below a rear portion of the head. A head harness (101) is attached to the mast for supporting the head from below the rear portion of the head.

41 Claims, 3 Drawing Sheets

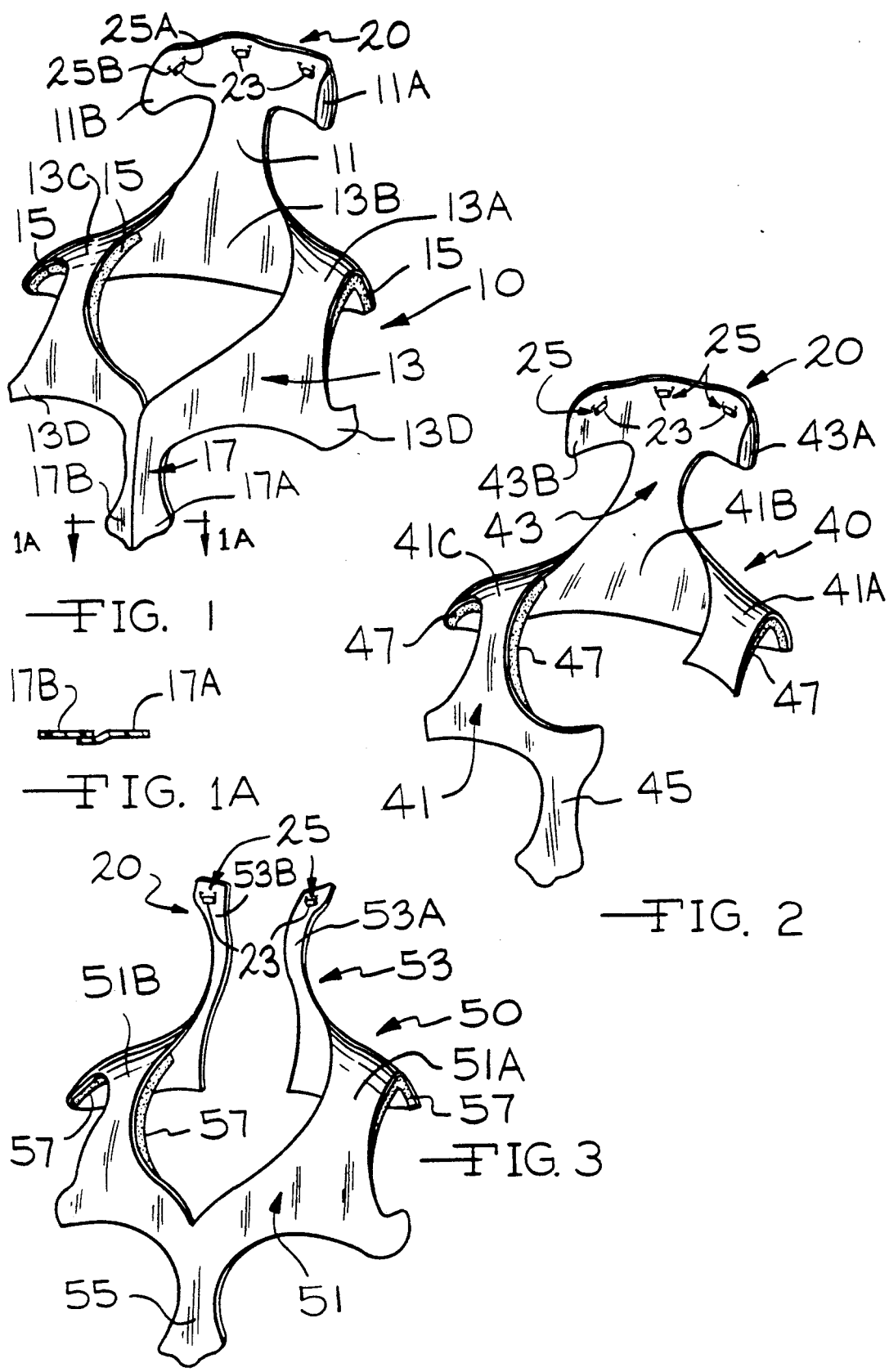

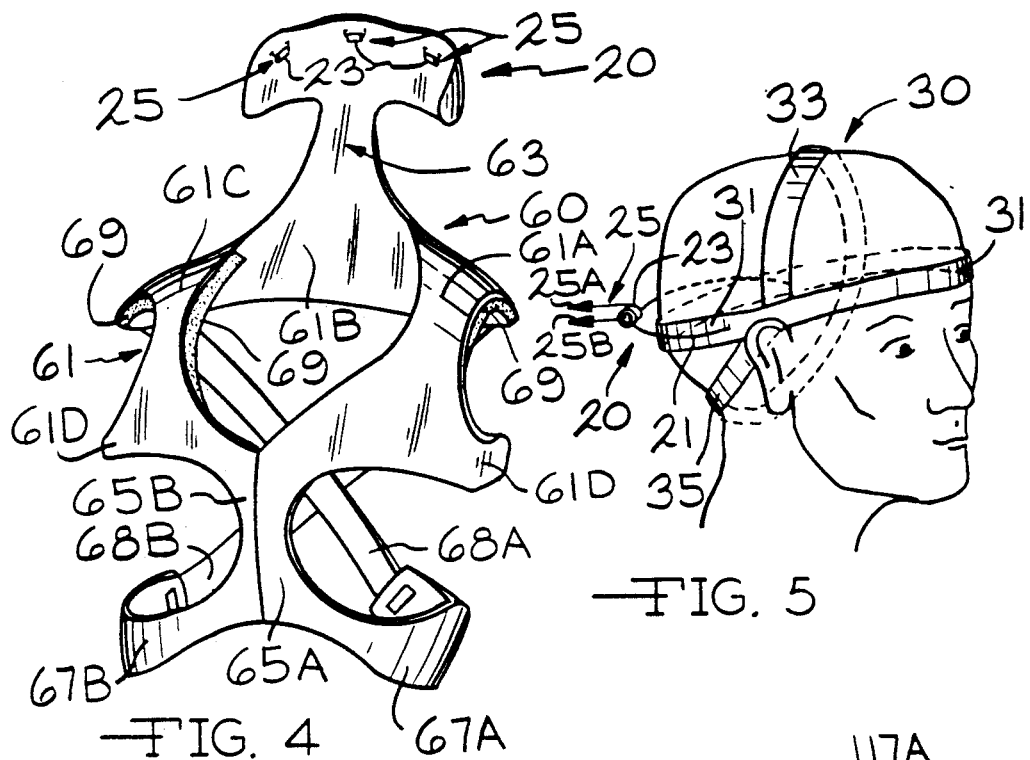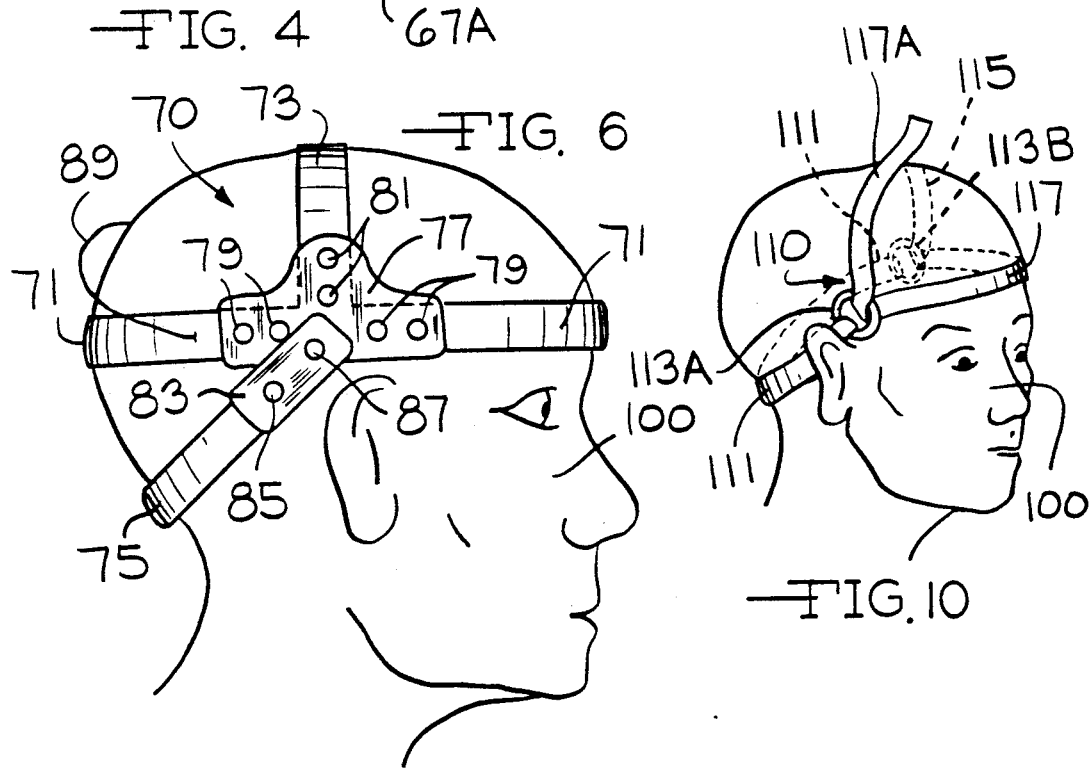

TETHERED MEDICAL RESTRAINT DEVICE

BACKGROUND OF THE INVENTION (1) Field of the Invention

The present invention relates to a head and neck support device for use by persons with a neck dysfunction. Neck dysfunction may result from congenital or acquired disease, trauma, or fatigue. In particular, the present invention relates to a medical restraining device which maintains a desired head position and which decreases neck loads by coupling the head and the torso. The device is comprised of a mast support that is secured to the upper torso and a mast member that extends upwards from the mast support to a position behind the neck and head of the user. One embodiment of the mast support is comprised of a yoke that is worn over the shoulders and the upper torso including the sternum. The mast is preferably attached by a tethering system to a harness as a head grasping apparatus that is worn circumferentially around the head. The head harness includes a forehead strap, a crown or top strap and a nape strap that extends over the nape of the neck. The head harness facilitates grasping the head so that supportive forces may be applied to the head through the tethers, connected between the head harness and the mast. The tethering system also partially transfers the weight of the head, held in the head harness, to the mast mounted on the mast support. That way, the head is supported on the torso, which helps to decrease neck loads, and the head is held to regulate anterior, posterior and sidewards head motion. The mast support is held to the body by a system of straps or by a wheelchair harness if the user is confined to a wheelchair. For cosmetic reasons, the mast support can be worn underneath clothing and a wig or hat can be worn to hide the head harness.

(2) Prior Art

Many persons suffer from neck dysfunction due to the effects of cervical spine trauma, diseases such as cerebral palsy, multiple sclerosis, and muscular dystrophy, or fatigue induced by environmental stress. The result of neck dysfunction is poor head control. The prior art has described various types of devices that relieve neck loads by supporting a person's head on their torso through the use of head rests, under chin supports, or various restraint devices which function by supporting the head and the torso with a rigid structure, connected to a seat in which the person is sitting. Head rests control rearward head motions, but do little to control forward and side motions of the head. Head support from below the jaw line does nothing to control rearward head motion while possibly creating difficulties in swallowing, breathing and sanitation. Devices which attempt to fix torso and head positions relative to a seating device fail because total body immobilization is impossible to achieve; inevitably, the torso will move in the seat and the neck is stretched as the head remains fixed relative to the seat. Moreover, none of the prior art devices were intended for daily use by persons suffering neck dysfunction from trauma or disease.

U.S. Pat. No. 3,170,659 to Wood, Jr. describes a head restraint for use in a space vehicle that has a curved rear head support with ear flaps pivotally hinged to each side of the head support. The head support is mounted to a frame connected to a seat or an integral part of the space vehicle. A forehead strap and a chin strap connect between the ear flaps. This invention permits the head to slide inside the rigid back rest and side flaps while the chin and forehead straps pivot and follow the head. That way, when loads are applied to the vehicle causing the occupant to move in the seat, the occupant's neck is not stretched. This device is somewhat complicated and requires that the crewman be occupying a seat.

U.S. Pat. No. 3,397,688 to Gottfried describes a pneumatically inflated neck and head stabilizer. The stabilizer device attempts to achieve total immobilization of the head and neck through use of armpit straps as a means of attaching the device to the torso. The immobilizer consists of a helmet or hood for enveloping a patient's head. The helmet is fabricated of sheet material having inflatable pockets that contact the head while the armpit harness holds the helmet in place. This immobilizer device is obtrusive and does not relieve normal load forces placed on the neck as the neck supports the head.

U.S. Pat. No. 3,522,804 to Towbin describes an infant's neck and head support that is intended to prevent spinal injuries of the hyperextension or "whiplash" type, caused by sudden and extreme movement of the head. The support is made of molded rubber and extends over the child's shoulders, back and chest. A head support, shaped to conform to the child's head, extends upwards along the back of the infant's neck and head and is reinforced by stiffening ribs. This device controls only rearward head motions and was intended to be worn continuously during the first four months of life. This device does not use a tethering system to control head motion and does not help to relieve normal load forces placed on the neck as the neck supports the head. Also, this device tends to make it difficult for an infant to swallow.

U.S. Pat. No. 4,339,151 to Riggs describes a head restraint for supporting the head while a user is seated in a chair. The head restraint has a strap that is wrapped around the back of a chair and an adjustable headband secured to a central, forward portion of the strap. The headband is worn on the user's head for supporting the head. This device requires that the user be seated in the chair, is very noticeable and the device does not relieve normal load forces placed on the neck as the neck supports the head.

U.S. Pat. No. 4,451,932 to Wagemann et al describes a device intended for use in infants, especially premature infants. The device functions to produce total, temporary restraint of all limbs and the head during extensive medical procedures. The device is also classified as an article of chill reducing clothing.

U.S. Pat. No. 4,718,412 to Nesbitt describes a single use, emergency care cervical immobilization means comprised of a lightweight cervical spine board made of wax coated or plastic coated reinforced double walled corrugated board. The device has pre-cut score lines for folding the device around the sides of the head and around the sides of the body to substantially enclose the wearer's neck and throat. The device is primarily used to immobilize the human head, neck and torso for use in emergency situations to prevent further injury to a potentially injured cervical spine.

U.S. Pat. No. 4,903,711 to Gunther describes a device for preventing infant colic and stomach discomfort. The device has a vest that is worn by the infant during feeding and burping. A bubble level is attached to the vest for visually indicating the position of the infant's torso with respect to vertical. This is a cumbersome device that completely encircles the neck and that is required to be worn externally over the infant's clothing.

U.S. Pat. No. 4,638,510 to Hubbard describes a device intended for use by occupants and drivers of high performance vehicles to reduce motions or loading in the neck and the upper torso when the vehicle experiences sudden deceleration or acceleration. The device has a stiff yoke worn over the upper torso of the occupant and a high collar that extends upwards from the yoke, with a set of tethers connected between the lateral and rear portions of a helmet and the collar. The collar extends upwards to adjacent the center of gravity of the head and helmet which is at about eye level of the occupant. The tethers allow needed head movement and yet reduce the potential for fatigue and crash injury by carrying forces that would otherwise be transmitted through the neck, thus reducing extreme motions of the head.

Other patents describe restraining devices that are mounted to a seat of a high performance vehicle and clasp the head of the occupant to limit head motion relative to the seat. These include U.S. Pat. No. 3,376,064 to Jackson; U.S. Pat. No. 3,922,034 to Eggert; U.S. Pat. No. 4,477,041 to Dunne; U.S. Pat. No. 4,664,341 to Cummings; British Patent No. 656,079 to Bower and British Patent No. 978,422 to Fitzgerald and Fisher.

Other U.S. patents distantly related to the present invention include U.S. Pat. No. 3,099,261 to Doss et al; U.S. Pat. No. 4,508,294 to Lorch and U.S. Pat. No. 4,592,523 to Herndon.

What is needed is a device that can be worn by both ambulatory people and people confined to a chair and that regulates anterior, posterior and sidewards head motion and that further helps to partially relieve neck loads by coupling the head with the torso. That way, when the load carrying capacity of the neck is altered by muscle fatigue, disease or through traumatic damage to the cervical vertibrae, the person is still able to maintain an acceptable head position during daily activities.

OBJECTS

It is therefore an object of the present invention to provide a device that maintains a desired head position and that partially decreases neck loads by coupling the head and the torso. Further, it is an object of the present invention to provide a head and neck stabilization device that provides head and neck support in persons unable to do so through their muscle strength and coordination, so that such persons are able to maintain acceptable head position during daily activities or transportation. Still further, it is an object of the present invention to provide a device that is worn beneath the clothing of both ambulatory persons and persons confined to a chair or seat and that helps to hold the head in an upright position to regulate anterior, posterior and sidewards head motion by coupling the head and the torso. Finally, it is an object of the present invention to provide a device for supporting the head and neck during daily activities that is relatively simple to construct and inexpensive to manufacture. These and other objects will become increasingly apparent by reference to the following description and to the drawings.

IN THE DRAWINGS

FIG. 1 is a front perspective view of a head and neck support device 10 of the invention, particularly illustrating a yoke 13 and an upwardly extending mast 11.

FIG. 1A is a cross-section along line 1A—1A of FIG. 1 showing the overlapping of sternum portions 17A and 17B of sternum plate 17.

FIG. 2 is a front perspective view of another embodiment of a head and neck support device 40 with a spaced apart right shoulder portion 41A and a sternum plate 45 for mounting the support device on a person from a side direction.

FIG. 3 is a front perspective view of another embodiment of a head and neck support device 50 with spaced apart right and left mast portions 53A and 53B for mounting the support device on a person from a frontal direction.

FIG. 4 is a front perspective view of an embodiment of a head and neck support device 60 with back straps 68A and 68B for use by ambulatory persons.

Figure 7:
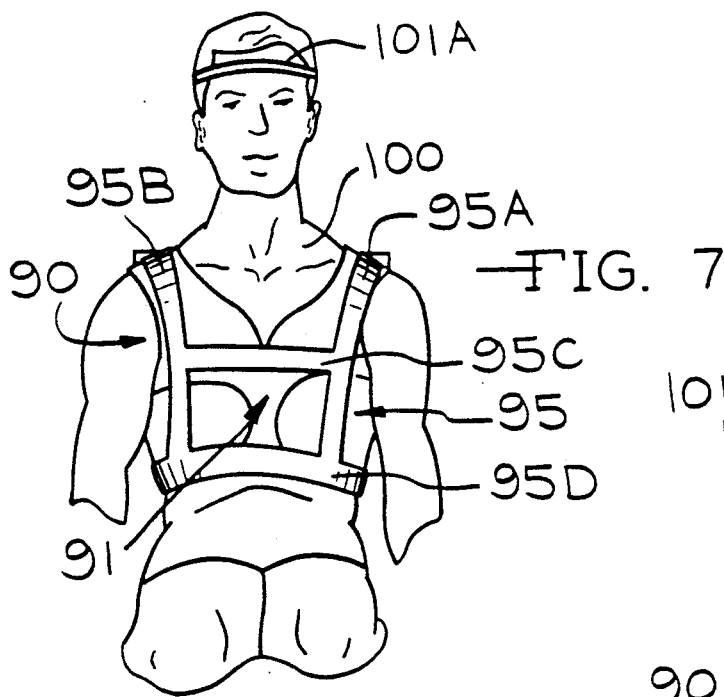

FIG. 5 is a left side schematic of a head harness 30 worn by a person 100 and showing a tether system 20 for use with the support devices of FIGS. 1 to 4.

FIG. 6 is a left side view of a head harness 70 worn by the person 100 and illustrating a head strap 71, a crown strap 73 and a nape strap 75.

FIG. 7 is a front view of a support device 90 shown mounted on the person 100 and connected to a head harness 101 for supporting the person's head from beneath a back portion of the head.

Figure 8:
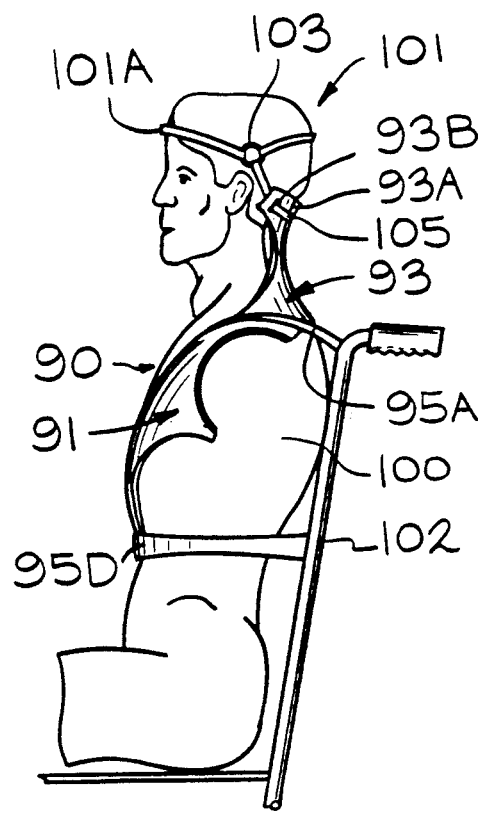
Figure 9:
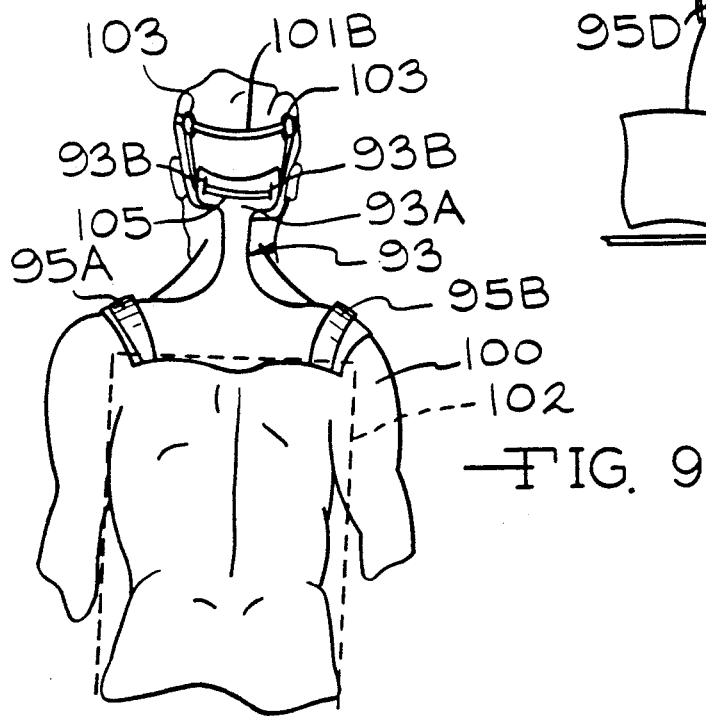

FIG. 8 is a side view of the support device 90 shown in FIG. 7 mounted on the person 100 seated in a wheelchair 102 and wearing the head harness 101 connected to the support device FIG. 9 is a back view of the support device 90 shown in FIG. 7 mounted on the person 100 seated in a wheelchair 102 and showing the head harness 101 connected to a mast 93.

FIG. 10 is a left side perspective view of a self-adjusting head harness 110 including a nape strap 111, a crown strap 115 and a forehead strap 117 with crown portion 117A for adjusting the head harness.

GENERAL DESCRIPTION

The present invention relates to a head support device to be worn by a person to maintain a desired head position and to decrease neck loads by coupling motions of the person's head, neck and torso, which comprises: a stiff support means, which is securable to the torso and having a portion of the support means extending behind the person to a position adjacent to and below the neck of the person; a stiff, mast means mounted on the support means so as to be close to the back of the neck of the person and extending upwards to a position adjacent a rear portion of the head; and a head harness means, which is securable around the head including a forehead portion and a nape portion extending over a nape section of the neck to provide a secure means of holding the head with the harness means attached to the mast means adjacent to the rear of the head.

Further, the present invention relates to a head support device to be worn by a person to maintain a desired head position and to decrease neck loads by coupling motions of the person's head, neck and torso, which comprises: a stiff, shoulder mounted yoke means having lateral, front and rear portions relative to the person, and which is contoured to be mounted over the torso of the person and adjacent to the neck; a stiff, mast means mounted on the yoke means so as to be close to the back of the neck of the person and extending upwards to a position adjacent a rear portion of the head; and a head harness means, which is securable around the head, including a forehead portion and a crown portion, a nape portion extending over a nape section of the neck to provide a secure means of holding the head with the harness means attached to the mast means adjacent to the rear of the head.

Further, the present invention relates to a head support device to be worn by a person to maintain a desired head position and to decrease neck loads by coupling the person's neck, head and torso which comprises: a stiff, shoulder mounted yoke means having lateral, front and rear portions relative to the person, and contoured to be mounted over the torso of the person and adjacent to the neck; a stiff, mast means mounted on the yoke means and extending upwards to a position adjacent to the center of gravity of the head; a head harness means, which is securable around the head including a forehead portion and a nape portion extending over a nape section of the neck to provide a secure means of holding the head; and a tether means connected between the head harness means and the mast means, adjacent to the center of gravity of the head to support the head in a desired position and to optionally support the weight of the head held by the head harness means through compression contact with the mast means.

Further, the present invention relates to a head support device to be worn by a person to maintain a desired head position and to decrease neck loads by coupling the person's head, neck and torso, which comprises: a stiff, shoulder mounted yoke means having lateral, front and rear portions relative to the person, and which is contoured to be mounted over the torso of the person and adjacent to the neck; a stiff, mast means mounted on the yoke means and extending upwards to a position adjacent a center of gravity of the head; a head harness means, which is securable around the head, including a forehead portion and a nape portion extending over a nape section of the neck to provide a secure means of holding the head; and a first fastening means secured to the head harness means with a tether means connected between the first fastening means and the mast means for supporting the head on the torso, wherein the tether means enables the head to rotate while the head is supported by the head harness means, with the head, which is held by the head harness means, supported through the first fastening means and the tether means by the mast means to maintain an acceptable head position by supporting the head on the torso.

Furthermore, the present invention relates to a head harness means for a head support device to be worn by a person to maintain a desired head position and to decrease neck loads by coupling the person's head, neck and torso, and comprising a stiff, support means, which is securable to the torso, and having a portion of the support means extending behind the person to a position adjacent to and below the neck of the person, and a stiff, mast means mounted on the support means and extending upwards to a position adjacent to the center of gravity of the head, which comprises: the head harness means to be mounted around the head including a forehead portion and a nape portion extending over a nape section of the neck to provide a secure means of holding the head, wherein a tether means is connected between the head harness means and the mast means, adjacent to the center of gravity of the head, to support the head in a desired position and to optionally support the weight of the head held by the head harness means through compression contact with the mast means.

Still further, the present invention relates to a head harness means for a head support device to be worn by a person to maintain a desired head position and to decrease neck loads by coupling the person's head, neck and torso, and comprising a stiff, shoulder mounted yoke means having lateral, front and rear portions relative to the person, and which is contoured to be mounted over the torso of the person and adjacent to the neck, and a stiff, mast means mounted on the yoke means and extending upwards to a position adjacent to the center of gravity of the head, which comprises: the head harness means to be mounted around the head including a forehead portion and a nape portion extending over a nape section of the neck to provide a secure means of holding the head, wherein a tether means is connected between the head harness means and the mast means adjacent to the center of gravity of the head, to support the head in a desired position and to optionally support the weight of the head held by the head harness means through compression contact with the mast means.

Further, the present invention relates to a method for providing a head support to maintain a desired head position and to decrease neck loads by coupling the person's head, neck and torso which comprises: securing a stiff support means to the torso and having a portion of the support means extending behind the person to a position adjacent to and below the neck of the person, with a stiff, mast means mounted on the support means and extending upwards to a position adjacent to the center of gravity of the head; and mounting a head harness means around the head, the head harness means including a forehead portion and a nape portion extending over a nape section of the neck and attached to the mast means adjacent to the rear portion of the head.

Furthermore, the present invention relates to a method for providing a head support to maintain a desired head position and to decrease neck loads by coupling the person's head, neck and torso which comprises: mounting a stiff, shoulder mounted yoke means over the torso of the person, the yoke means having lateral, front and rear portions relative to the person and adjacent to the neck, with a stiff, mast means mounted on the yoke means and extending upwards to a position adjacent to the center of gravity of the head; and mounting a head harness means around the head, the head harness means including a forehead portion and a nape portion extending over a nape section of the neck and attached to the mast means adjacent to the rear portion of the head.

Still further, the present invention relates to a head harness for use by a person wearing a stiff, shoulder mounted yoke means having lateral, front and rear portions relative to the person and contoured to be mounted over the torso of the person and adjacent to the neck, and with a stiff, mast means mounted on the yoke means and extending upwards to a position adjacent to the center of gravity of the head, which comprises: the head harness means mounted around the head including a forehead portion, and a nape portion extending over a nape section of the neck; and a tether means for connection between a first fastening means secured to the head harness means and the mast means for supporting the head on the torso, wherein the tether means enables the head to rotate while supporting the head in a desired position by the head harness means, with the head, which is held by the head harness means, supported through the first fastening means and the tether means by the mast means to help relieve neck loads by supporting the head on the torso.

Finally, the present invention relates to a head support device to be worn by a person to maintain a desired head position and to decrease neck loads by coupling motions of the person's head, neck and torso which comprises: a stiff, shoulder mounted yoke means having lateral, front and rear portions relative to the person, and contoured to be mounted over the torso of the person and adjacent to the neck; a stiff, mast means mounted on the yoke means with an upper portion of the mast means adjacent to a nape section of the neck and below the center of gravity of the head; and a head harness means, which is securable around a circumferential extent of the head and including a forehead portion, wherein the head harness means is attached to the mast means so that the head is optionally supported on the mast means with the upper portion of the mast means contacting the head, adjacent to the nape of the neck and adjacent and below the center of gravity of the head.

SPECIFIC DESCRIPTION

FIG. 1 shows a support device 10 adapted to be worn on the torso by a person 100 suffering from neck dysfunction to support the head and neck on the torso so that the head is maintained in an upright position for daily activities. The support device 10 comprises a stiff mast 11, which has a limited ability to flex, and that extends from a mast support means mounted on the torso and particularly shown as a yoke 13. The mast 11 is preferably made from a metal material while the yoke 13 is preferably made of a resilient, plastic material. The mast 11 can also be made of a stiff, plastic material, having a limited ability to flex, In this case, the mast 11 and yoke 13 are preferably molded as an integral unit. If the mast 11 is a metal member, the mast 11 is preferably secured to the yoke 13 by bolts (not shown) or other suitable securing means.

The yoke 13 is contoured to fit over the upper torso of the person 100, including the rib cage and shoulders and includes a right shoulder portion 13A, a back portion 13B and a left shoulder portion 13C with armpit tabs 13D for added stability. Padding 15 is included to provide a comfortable fit for the person 100. To provide added stability on the torso, sternum plate 17 depends over the sternum. The mast 11 extends upwards from the back section 13B of the yoke 13, to a height approximately equal to the center of gravity of the person's 100 head (approximately eye level). At its upper extent, the mast 11 bifurcates into spaced apart right and left ear portions 11A and 11B positioned adjacent to and behind the person's 100 right and left ears, respectively. Mounted on the mast 11, including the portions 11A and 11B, is a tether system 20 for attaching the support device 10 to a head harness (not shown) as a head grasping apparatus, to support the head and neck on the torso. The tether system 20 will be described in detail hereinafter with respect to a head harness 30 as shown in FIG. 5.

The sternum plate 17 has right and left portions 17A and 17B respectively, that overlap as shown in FIG. 1A. To mount the support device 10 on the person 100, a helper grasps the support device 10 between the sternum plate 17 and each of the armpit tabs 13D and separates the portions 17A and 17B of the sternum plate 17 a distance sufficient to slip the portions 17A and 17B over the neck of the person 100. The yoke 13 is then mounted over the shoulders and the upper torso of the person 100. Once the yoke 13 is mounted on the person 100, the resilient plastic material of the yoke 13 assumes its original shape with the sternum portions 17A and 17B returning to their original overlapped configuration (FIG. 1A).

FIG. 5 is a schematic showing the tethering system 20 for connecting the head harness 30 to the mast 11 of the support device 10, shown in FIG. 1. The tethering system 20 is also shown mounted on the support devices 40, 50 and 60 shown in FIGS. 2 to 4. As shown in FIG. 5, the head harness 30 is comprised of a head strap 31, a crown strap 33 and a nape strap 35. When the head harness 30 is coupled to the support device 10 (FIG. 1) by the tethering system 20, the tethering system 20 enables the head to swivel independently on the torso while maintaining the head in an upright and erect position. Thus, the support device 10 supports the head on the torso by grasping the head in the head harness 30 and holding the head in an upright position to regulate anterior, posterior and sidewards head motion. At the same time, the support device 10 transfers some of the weight of the head through the tethering system 20 to the mast 11 and the yoke 13. This helps to partially relieve load forces on the neck resulting from the weight of the head.

As shown in FIG. 5, the tethering system 20 is comprised of a slider line 21 having spaced apart ends mounted to the head strap 31 adjacent to and behind the ears of the person 100. A slide block 23 slides on the slider line 21 and allows the person 100 to turn her head as the slide block 23 slides on the line 21. A tether line 25 is fixably mounted to the slide block 23. The tether line 25 has spaced apart ends 25A and 25B which are mounted to the mast 11 (FIG. 1). The preferred embodiment provides for a plurality of tether lines 25 connected from the mast 11 to the slider line 21 by slide blocks 23. At least one tether line 25 with slide block 23 is connected to each portion 11A and 11B of the mast 11 with a third tether line 25 and slide block 23 attached to the mast 11, directly behind a back portion of the head. If more head support is desired, more tether lines 25 with slide blocks 23 can be used. The tether line 25 can provide any desired degree of head mobility from total immobilization to loose support, to hold the head in an upright and erect position. The tethering system 20 also helps to partially decrease neck loads by coupling the head supported in the head harness 30 through compressive contact with the mast 11 and tension in the tether system 30.

Also, the slide block 23 can be fixably mounted to the slider line 21 to slide on the tether line 25. Or, the slider block 23 could slide with respect to both the slider line 21 and the tether line 25. What is important is that the slider line 21, block 23 and tether line 25 provide for movement of the head relative to the torso while supporting the head in an upright position in conjunction with the head harness 30 tethered to the torso through the mast 11 and yoke 13.

FIG. 2 shows another preferred embodiment of a support device 40 of the present invention that is used with the tethering system 20 and head harness 30 shown in FIG. 5. The support device 40 includes a yoke 41 and mast 43. The yoke 41 is shaped to slip over the neck of the person 100 from a side direction, to mount the yoke 41 on the upper torso. The yoke 41 comprises a right shoulder portion 41A, a back portion 41B, a left shoulder portion 41C and a sternum plate 45. The right shoulder portion 41A and the sternum plate 45 are spaced apart. This provides for side mounting the yoke 41 onto the torso of the person 100. The integral mast 43 extends from the back portion 41B in a manner similar to the mast 11 mounted on the yoke 13 (FIG. 1) and bifurcates into right and left ear portions 43A and 43B. Padding 47 is included to provide a comfortable fit for the person 100. The yoke 41 is then secured to the torso of the person 100 with a torso harness (not shown).

FIG. 3 shows still another preferred embodiment of a support device 50 of the present invention that is used with the tethering system 20 and head harness 30 (FIG. 5). The support device 50 includes a yoke 51 and mast 53. The yoke 51 is shaped to slip over the neck of the person 100 from a frontal direction, to mount the yoke 51 on the upper torso. The yoke 51 is comprised of right and left shoulder portions 51A and 51B joined by a central sternum plate 55. The right and left shoulder portions 51A and 51B are spaced apart, opposite the sternum plate 55. This provides for mounting the yoke 51 on the person 100 from the front. Right and left mast portions 53A and 53B extend from the right and left shoulder portions 51A and 51B, respectively, spaced from the sternum plate 55 to form an integral unit. Padding 57 is included to provide a comfortable fit for the person 100. The yoke 51 is then secured to the torso of the person 100 with a torso harness (not shown).

FIG. 4 shows still another preferred embodiment of a support device 60 of the present invention that is used with the tethering system 20 and head harness 30 (FIG. 5). The support device 60 includes a yoke 61 and a stiff mast 63. The support device 60 is preferably worn by ambulatory people. The yoke 61 is contoured to fit over the torso of the person 100 and includes a right shoulder portion 61A, a back portion 61B and a left shoulder portion 61C with armpit tabs 61D for added stability. A sternum plate 65 comprised of right and left sternum portions 65A and 65B, depends over the sternum to the stomach. The sternum portions 65A and 65B overlap in a similar manner to that shown in FIG. 1A for sternum portions 17A and 17B. Stiff waist extensions 67A and 67B extend from the lower ends of the sternum portions 65A and 65B, respectively. The waist extensions 67A and 67B are contoured to mount substantially around the girth of the person 100 and extend to a position adjacent to the small of the back. Back straps 68A and 68B are connected between the ends of the waist extensions 67A and 67B and opposite shoulder portions 61C and 61A of the yoke 61, respectively, in an X-shaped configuration. Padding 69 is included to provide a comfortable fit for the person 100.

To mount the support device 60 on the person 100, a helper grasps the support device 60 between the sternum portions 65A and 65B of the sternum plate 65 and each of the shoulder portions 61A and 61B, respectively, to separate the sternum plate portions 65A and 65B a distance sufficient to slip the portions 65A and 65B over the neck of the person 100. The yoke 61 is then mounted over the shoulders and the torso with the waist extensions 67A and 67B extending over the girth of the person 100. The back straps 69A and 69B are then tightened by a conventional adjusting means (not shown) mounted on the straps 69A and 69B so that the yoke 61 is securely mounted on the torso. It is preferred that the sternum plate portions 65A and 65B be provided with a conventional fastening means (not shown) so that the portions 65A and 65B do not separate when the strap 69A and 69B are tightened.

FIG. 6 shows another preferred embodiment of a head harness 70 that is sized to the head of the person 100. The head harness 70 is comprised of a head strap 71 extending around the circumferential extent of the head, a crown strap 73 that extends over the crown of the head and a nape strap 75 that mounts over the nape of the neck. Mounting plates 77 are secured to the head strap 71 above the ears (only one plate 77 is shown above the right ear) by rivets 79 or other suitable fastening means. The crown strap 73 is secured to the mounting plate 77 by rivets 81 or other suitable fastening means. The straps 71, 73 and 75 are flexible and are made of plastic or a reinforced cloth material or any other suitable material. The mounting plate 77 and the rivets 79 and 81 are preferably made of plastic or any other suitable material. The spaced apart ends of the nape strap 75 are mounted to nape plates 83 by rivets 85 (only the nape plate 85 adjacent the right ear is shown) and the nape plates 83 are pivotally mounted to the mounting plates 77 by rivets 87. Pivotally mounting the nape plates 83 to the mounting plates 77 enables the nape strap 75 to be comfortably positioned on the person's 100 neck although the head harness 70 must be fitted to the person's 100 specific head size. That way, the head harness 70 fits over the head so as to cradle the head without being so tight and uncomfortable as to cause the person 100 to experience headaches or head pain. The head harness 70 is completed by a slider line 89 mounted to the head strap 71 adjacent to and behind each ear (one end of the line 89, secured behind the right ear is shown). The slider line 89 is similar to the slider line 21 shown in FIG. 5 and serves to attach the head harness 70 to the tether system 20 shown in FIGS. 1 to 4.

The head harness 70 shown in FIG. 6 can also be an adjustable harness. In this embodiment, instead of securing the head strap 71, the crown strap 73 and the nape strap 75 to the mounting plate 77 and the nape plate 83 by rivets 79, 81 and 85, respectively, the fastening means can include a conventional male and female snap construction (not shown). In this construction, the mounting plate 77 and the nape plate 83 are provided with male snaps that mate with female openings spaced uniformly along the length of the straps 71, 73 and 75. This enables the head harness 70 to be adjustable so that it can be worn by people having various head sizes.

FIGS. 7 to 9 show another embodiment of a support device 90 for supporting the head from below a rear or back portion of the head. The support device 90 includes a yoke 91 contoured and mounted over the upper torso of the person 100 as has been described above. A mast 93, integral with the yoke 91, extends upward to an arcuate portion 93A that mounts beneath the back portion of the head. The yoke 91 is fastened to the person 100 with a conventional torso harness 95 comprised of shoulder belts 95A and 95B mounted on the chair 102 and positioned in grooves or slots 91A on either side of and over the yoke 91 to hold the yoke 91 against the torso of the person 100. The shoulder belts 95A and 95B are joined together with a chest belt 95C and a waist belt 95D that straps around the waist of the person 100 and is secured to the chair 102 (FIG. 8).

As shown in FIGS. 7 to 9, the support device 90 is completed by a head harness 101. The head harness 101 is worn over the head of the person 100 and extends over the nape of the person's 100 neck. This serves to maintain the head in an acceptable position during daily activities. The head harness 101 is comprised of a forehead strap 101A and a back head strap 101B connected by a pair of O-rings 103 mounted adjacent to and above the ears. A support strap 105 connects between the O-rings 103. The support strap 105 is permanently secured to one of the O-rings 103 and adjustably secured to the other of the O-rings 103. That way, the support strap 105 is able to be threaded through openings 93B adjacent to the right and left ears in the arcuate portion 93A of the mast 93 for connecting the head harness 101 to the mast 93 and yoke 91 of the support device 90. The support device 90 holds the head erect when support strap 105 is threaded through the openings 93B in the arcuate portion 93A of the mast 93 to draw the head held by the head harness 101 to the mast 93. The head is thus supported with the back of the head resting on an upper portion of the arcuate portion 93A as shown in FIGS. 8 and 9. If the person 100 wants to see in a lateral direction, the person 100 must turn their torso (if possible) because the support device 90 couples the movements of the torso with the head.

FIG. 10 shows another preferred embodiment of a self-adjusting head harness 110 of the present invention. Head harness 110 is comprised of a nape strap 111 that extends over the nape of the neck with spaced apart ends secured to right and left O-rings 113A and 113B mounted adjacent to and above the right and left ears, respectively. A crown strap 115 is mounted over the crown or top of the head and extends between the O-rings 113A and 113B. An adjustable forehead strap 117 is secured to the left O-ring 113B and extends across the forehead of the person 100 to the right O-ring 113A. A crown portion 117A of the forehead strap 117 extends through the right O-ring 113A and has a sufficient amount of length to extend up and over the crown strap 115. The crown portion 117A of the forehead strap 117 and the crown strap 115 are provided with VELCRO or some other suitable fastening means for securing the crown portion 117A of the forehead strap 117 to the crown strap 115. In this manner, the head harness 110 is adjustable to fit persons 100 having different head sizes. To adjust the head harness 110, the crown portion 117A of the forehead strap 117 is unfastened from the crown strap 115 and the forehead strap 117A is either loosened or tightened to fit the person 100. The crown portion 117A is then resecured to the crown strap 115 by fastening the crown portion 117A to the crown strap 115 with the fastening means.

It is contemplated that head harness 110 can be used with the support device 90 as shown in FIGS. 7 to 9. In that manner, the nape strap 111 is permanently secured to one of the O-rings 113A and adjustably secured to the other O-ring 113B. To secure the head harness 110 to the support device 90 shown in FIGS. 7 to 9, the head harness 110 is first fitted to the person's 100 head by adjusting crown portion 117A of the forehead strap 117 and the crown strap 115 with the fastening means. The support device 90 is mounted on the person's 100 torso and the nape strap 111 is threaded through the openings 93B in the mast 93 and secured to the O-ring 113B.

IN USE

The support device 10 as shown in FIG. 1 is mounted on the person 100 with the yoke 13 mounted over the upper torso including the shoulders. The neck area is left open to allow for medical treatment, swallowing and personal hygiene. The yoke 13 is preferably contoured to the shape of the person 100 and is padded to ensure a comfortable fit. If the person 100 is confined to a wheelchair (not shown) a torso harness 95 as shown in FIGS. 7 to 9 can be used with the yoke 13. If the person 100 is ambulatory, the yoke 61 of the support device 60 shown in FIG. 4 can be mounted on the person's 100 torso with back straps 69A and 69B.

To partially relieve neck loads resulting from the weight of the head supported on the neck, in addition to maintaining the head in an erect position, head harness 30 (FIG. 5) can be used with a mast 11 and yoke 13 as shown in FIG. 1 or with the support devices 40, 50 and 60 shown in FIGS. 2 to 4. The head harness 30 is mounted on the head as described above. The mast 11 of support device 10 extends behind the neck and the back of the head to a point above the center of gravity of the head (approximately eye level). The weight of the head is carried by the nape strap 35 and the forehead strap 31 while the crown strap 33 serves to keep the head harness 30 from slipping on the head.

A plurality of tether lines 25 with slider blocks 23 of the tether system 20 are preferably mounted on the mast 11 between the right and left portions 11A and 11B as shown in FIG. 1 or to the masts 43, 53 and 63 shown in FIGS. 2 to 4, respectively. One end of the slider line 21 is preferably fixably secured to the head strap 31 while the other end is adjustably secured to the head strap 31. To attach the head harness 30 to the support device 10, one end of the slider line 21 is unfastened from the head strap 31 and the line 21 is threaded through the slider blocks 23 of the tether system 20. The adjustable end of the slider line 21 is then secured to the head strap 31 to connect the head harness 30 to the support device 10. The head harness 30 enables the head to swivel independently of the torso, with the slider line 21 sliding on the slider blocks 23 mounted on the tethers 25 and connected to the mast 11. Variations in the tension of the tether lines 25 between the slider line 21 and the mast 11 provide any desired degree of head mobility from almost total immobilization to loose support. Also, for cosmetic reasons, the head harness 30 can be used in conjunction with a wig, sweatband or cap and the yoke 13 can be worn underneath outer clothing. If additional protection is desired, the head harness 30 may be incorporated into a helmet (not shown). An optional chin strap (not shown) may also be desirable for some people.

It is intended that the foregoing description be only illustrative of the present invention and that the present invention be limited only by the hereinafter appended claims.

I claim:

1. A head support device to be worn by a person to maintain a desired head position and to decrease neck loads by coupling motions of the person's head, neck and torso, which comprises:
   (a) a stiff support means, which is securable to the torso and having a portion of the support means adapted to extend behind the person to a position adjacent to and below the neck of the person;
   (b) a stiff, mast means mounted on the support means so as to be close to the back of the neck of the person and adapted to extend upwards to a position adjacent a rear portion of the head;
   (c) a head harness means separate from the mast means, which is securable around the head including a forehead portion and a nape portion adapted to extend over a nape section of the neck to provide a secure means of holding the head with the harness means attached by a tether means to the mast means adjacent to the rear of the head.

2. The support device of claim 1 wherein the head harness means is attached to the mast means by the tether means connected to the mast means adapted to be adjacent to the center of gravity of the head, to support the head in a desired position and to optionally support the weight of the head held by the head harness means through compression contact with the mast means.

3. The support device of claim 1 wherein the mast means and the yoke means are integral.

4. The support device of claim 1 wherein the head harness means is provided with a crown strap having spaced apart ends that attach to the head harness means adjacent to each of the sides of the head of the person wherein the crown strap is adapted to mount on a top portion of the head.

5. A head support device to be worn by a person to maintain a desired head position and to decrease neck loads by coupling motions of the person's head, neck and torso, which comprises:
  (a) a stiff, shoulder mounted yoke means having lateral, front and rear portions which is contoured to be mounted over the torso of the person and adjacent to the neck;
  (b) a stiff, mast means mounted on the yoke means adapted to be close to the back of the neck of the person and adapted to extend upwards to a position adjacent a rear portion of the head;
  (c) a head harness means separate from the mast means, which is securable around the head, including a forehead portion and a nape portion adapted to extend over a nape section of the neck to provide a secure means of holding the head with the harness means attached by a tether means to the mast means adjacent to the rear of the head.

6. The support device of claim 5 wherein the head harness means is attached to the mast means by the tether means connected to the mast means adapted to be adjacent to the center of gravity of the head, to support the head in a desired position and to optionally support the weight of the head held by the head harness means through compression contact with the mast means.

7. The support device of claim 5 wherein the mast means and the yoke means are integral.

8. A head support device to be worn by a person to maintain a desired head position and to decrease neck loads by coupling the person's head, neck and torso, which comprises:
  (a) a stiff, shoulder mounted yoke means having lateral, front and rear portions which is contoured to be mounted over the torso of the person and adjacent to the neck;
  (b) a stiff, mast means mounted on the yoke means and adapted to be close to the back of the neck of the person and adapted to extend upwards to a position adjacent a center of gravity of the head adjacent a rear portion of the head;
  (c) a head harness means, which is securable around the head, including a forehead portion and a nape portion adapted to extend over a nape section of the neck to provide a secure means of holding the head; and
  (d) a tether means connected between the head harness means and the mast means adjacent to the rear of the head and adapted to be adjacent to the center of gravity of the head to support the head in a desired position and to optionally support the weight of the head held by the head harness means through compression contact with the mast means.

9. The device of claim 8 wherein the tether means is adapted to enable the head to rotate.

10. The device of claim 8 wherein the mast means and the yoke means are integral.

11. The device of claim 10 wherein the mast means and the yoke means are made of a plastic material.

12. The device of claim 8 wherein the yoke means is provided with a pad means to cushion the yoke means on the torso.

13. A head support device to be worn by a person to maintain a desired head position and to decrease neck loads by coupling the person's head, neck and torso, which comprises:
  (a) a stiff, shoulder mounted yoke means having lateral, front and rear portions which is contoured to be mounted over the torso of the person and adjacent to the neck;
  (b) a stiff, mast means mounted on the yoke means and adapted to be close to the back of the neck of the person and to extend upwards to a position adjacent a center of gravity of the head adjacent a rear portion of the head;
  (c) a head harness means, which is securable around the head, including a forehead portion and a nape portion adapted to extend over a nape section of the neck to provide a secure means of holding the head; and
  (d) a first fastening means secured to the head harness means with a tether means connected between the first fastening means and the mast means adjacent to the rear of the head for supporting the head on the torso, wherein the tether means enables the head to rotate while the head is supported by the head harness means, with the head which is held by the head harness means, supported through the first fastening means and the tether means by the mast means, to maintain an acceptable head position by supporting the head on the torso.

14. The device of claim 13 wherein the first fastening means is secured to the head harness means on a strap portion of the head harness means mounted on the rear portion of the head adapted to be adjacent the center of gravity of the head.

15. The device of claim 13 wherein a sternum portion of the yoke means adapted to extend over a sternum of the person.

16. The device of claim 15 wherein the yoke means separates along a seam through the sternum portion for fitting the yoke means to the person from a direction behind the person.

17. The device of claim 15 wherein the yoke means is provided with an opening through the rear portion for fitting the yoke means to the person from a direction in front of the person.

18. The device of claim 13 wherein the yoke means is provided with strap means for securing the yoke means on the torso of the person.

19. The device of claim 18 adapted for the person seated in a wheelchair or seating system with the strap means secured to the wheelchair or seating system to confine the person in the wheelchair or seating system and wherein the strap means extend to the yoke means mounted on the torso of the person.

20. The device of claim 13 wherein the yoke means is integral with the mast means and wherein the yoke means and the mast means are constructed of a plastic material.

21. The device of claim 13 wherein the tether means extends through a slide means secured to the first fastening means, the slide means allowing for relative sliding movement of the first fastening means secured to the head harness means and the tether means to enable the person to rotate their head about the neck to provide for the forward and lateral fields of vision.

22. A head harness means for a head support device to be worn by a person to maintain a desired head position and to decrease neck loads by coupling the person's head, neck and torso, and comprising a stiff, support means, which is securable to the torso, and having a portion of the support means adapted to extend behind the person to a position adjacent to and below the neck of the person, and a stiff, mast means mounted on the support means and adapted to extend upwards to a position adjacent a center of gravity of the head and adjacent a rear portion of the head, which comprises:
  (a) the head harness means adapted to be mounted around the head including a forehead portion and a nape portion adapted to extend over a nape section of the neck to provide a secure means of holding the head, and adapted for connection with a tether means connected between the head harness means and the mast means adjacent to the rear of the head and which is to be adjacent to the center of gravity of the head, to support the head in a desired position and to optionally support the weight of the head held by the head harness means through compression contact with the mast means.

23. The head harness means of claim 22 wherein the tether means enables the head to rotate while maintaining a predetermined head position by supporting the head held by the head harness means on the mast means and support means mounted on the torso.

24. A head harness means for a head support device to be worn by a person to maintain a desired head position and to decrease neck loads by coupling the person's head, neck and torso, and comprising a stiff, shoulder mounted yoke means having laterals, front and rear portions relative to the person, and which is contoured to be mounted over the torso of the person and adjacent to the neck, and a stiff, mast means mounted on the yoke means and adapted to extend upwards to a position adjacent a center of gravity of the head, which comprises:
  (a) the head harness means to be mounted around the head including a forehead portion and a nape portion adapted to extend over a nape section of the neck to provide a secure means of holding the head, and adapted for connection with a tether means connected between the head harness means and the mast means which is to be adjacent to the center of gravity of the head, to support the head in a desired position and to optionally support the weight of the head held by the head harness means through compression contact with the mast means.

25. The head harness means of claim 24 wherein the tether means enables the head to rotate while maintaining a predetermined head position by supporting the head held by the head harness means on the mast means and yoke means mounted on the torso.

26. The head harness means of claim 24 wherein the mast means and the yoke means are integral.

27. The head harness means of claim 26 wherein the mast means and the yoke means are made of a plastic material.

28. The head harness means of claim 24 wherein the yoke means is provided with a pad means to cushion the yoke means on the torso.

29. A method for providing a head support to maintain a desired head position and to decrease neck loads by coupling the person's head, neck and torso which comprises:
  (a) securing a stiff support means to the torso and having a portion of the support means extending behind the person to a position adjacent to and below the neck of the person, with a stiff, mast means mounted on the support means and adapted to extend upwards to a position adjacent a center of gravity of the head; and
  (b) mounted a head harness means around the head, the head harness means including a forehead portion and a nape portion adapted to extend over a nape section of the neck and attached by a tether means to the mast means adjacent to the rear portion of the head.

30. The method of claim 29 wherein the head harness means is attached to the mast means by tether means connected between the mast means and a first fastening means secured to the head harness means adapted to be adjacent to the center of gravity of the head, to support the head in a desired position, and to optionally support the weight of the head held by the head harness means through compression contact with the mast means.

31. The method of claim 30 wherein the tether means extends through a slide means secured to the first fastening means, the slide means allowing for relative sliding movement of the first fastening means secured to the head harness means and the tether means to enable the person to rotate their head about the neck.

32. A method for providing a head support to maintain a desired head position and to decrease neck loads by coupling the person's head, neck and torso which comprises:
  (a) mounting a stiff, shoulder mounted yoke means over the torso of the person, the yoke means having lateral, front and rear portions relative to the person and adjacent to the neck, with a stiff, mast means mounted on the yoke means and extending upwards to a position adjacent a center of gravity of the head; and
  (b) mounting a head harness means separate from the mast means around the head, the head harness means including a forehead portion and a nape portion extending over a nape section of the neck and attached to the mast means by a tether means adjacent to the rear portion of the head.

33. The method of claim 32 wherein the head harness means is attached to the mast means by the tether means connected between the mast means and a first fastening means secured to the head harness means adapted to be adjacent to the center of gravity of the head, to support the head in a desired position and to optionally support the weight of the head held by the head harness means through compression contact with the mast means.

34. The method of claim 33 wherein the tether means extends through a slide means secured to the first fastening means, the slide means allowing for relative sliding movement of the first fastening means secured to the head harness means and the tether means to enable the person to rotate their head about the neck.

35. A head harness means for use by a person wearing a stiff, shoulder mounted yoke means having lateral, front and rear portions relative to the person and contoured to be mounted over the torso of the person and adjacent to the neck, and with a stiff, mast means mounted on the yoke means and adapted to extend upwards to a position adjacent a center of gravity of the head and adjacent a rear portion of the head, which comprises:

(a) the head harness means mounted around the head including a forehead portion and a nape portion adapted to extend over a nape section of the neck; and (b) a tether means adapted for connection between a first fastening means secured to the head harness means and adapted for connection to the mast means adjacent to the rear portion of the head for supporting the head on the torso, wherein the tether means enables the head to rotate while supporting the head in a desired position by the head harness means, with the head, which is held by the head harness means, supported through the first fastening means and tether means by the mast means to help relieve neck loads by supporting the head on the torso.

36. The head harness of claim 35 wherein the tether means extends through a slide means secured to the first fastening means, the slide means allowing for relative sliding movement of the first fastening means secured to the head harness means and the tether means to enable the person to rotate their head about the neck.

37. The head harness of claim 35 wherein an upper extent of the mast means provides for an arcuate portion that is adapted to extend around the rear portion of the head, the arcuate portion having spaced apart ends adjacent to each side of the head of the person, wherein at least one of the tether means having opposed ends is connected between the first fastening means and the mast means with the opposed ends of the tether means mounted to the arcuate portion between the spaced apart ends of the arcuate portion for maintaining an acceptable head position by supporting the head held in the head harness means on the torso.

38. The head harness of claim 37 wherein there is at least one tether means connected between the first fastening means and the arcuate portion of the mast means adjacent to each side of the head and adjacent to the rear portion of the head.

39. The head harness of claim 35 wherein the yoke means is provided with strap means and wherein the harness is adapted for the person seated in a wheelchair or seating system with the strap means secured to a frame portion of the wheelchair or seating system to confine the person in the wheelchair or seating system and wherein the strap means extend to the yoke means mounted on the torso of the person.

40. A head support device to be worn by a person to maintain a desired head position and to decrease neck loads by coupling motions of the person's head, neck and torso which comprises:

(a) a stiff, shoulder mounted yoke means having lateral, front and rear portions which is contoured to be mounted over the torso of the person and adjacent to the neck;

(b) a stiff, mast means mounted on the yoke means with an upper portion of the mast means adapted to be adjacent to a nape section of the neck and below a center of gravity of the head; and (c) a head harness means separate from the mast means, which is securable around a circumferential extent of the head, and including a forehead portion, wherein the head harness means is attached to the mast means by a tether means adjacent to the rear of the head and so that the head is optionally supported on the mast means with the upper portion of the mast means contacting the head, adjacent to the nape of the neck and adjacent below the center of gravity of the head.

41. The device of claim 40 wherein the head harness means has a strap portion with spaced apart ends adapted to extend from the forehead portion adjacent to each of the sides of the head of the person and wherein the strap portion is adapted to be secured to the upper portion of the mast means adjacent to the nape of the neck to provide for attaching the head harness means to the mast means.

* * * * *